(12) United States Patent
Hogendijk (10) Patent No.: US 7,033,336 B2
(45) Date of Patent: Apr. 25, 2006

(54) PROXIMAL CATHETER ASSEMBLY HAVING A RELIEF VALVE

(75) Inventor: Michael Hogendijk, Palo Alto, CA (US)

(73) Assignee: Gore Enterprise Holdings, Inc., Newark, DE (US)

( * ) Notice: Subject to any disclaimer, the term of this patent is extended or adjusted under 35 U.S.C. 154(b) by 390 days.

(21) Appl. No.: 10/138,013

(22) Filed: May 1, 2002

(65) Prior Publication Data

US 2003/0187392 A1 Oct. 2, 2003

Related U.S. Application Data

(63) Continuation-in-part of application No. 10/112,807, filed on Mar. 29, 2002, now Pat. No. 6,960,189.

(51) Int. Cl.
*A61M 1/00* (2006.01)
*A61M 5/00* (2006.01)

(52) U.S. Cl. .................... 604/119; 604/246; 604/35

(58) Field of Classification Search .................. 604/35, 604/118, 119, 121, 246–250, 129, 500
See application file for complete search history.

(56) References Cited

U.S. PATENT DOCUMENTS

| | | | |
|---|---|---|---|
| 4,230,128 A | 10/1980 | Aramayo | |
| 4,397,335 A | 8/1983 | Doblar et al. | |
| 4,595,005 A | 6/1986 | Jinotti | |
| 4,642,097 A | 2/1987 | Siposs | |
| 4,680,026 A | 7/1987 | Weightman et al. | |
| 4,708,717 A | 11/1987 | Deane et al. | |
| 4,850,350 A * | 7/1989 | Jackson | 128/207.16 |
| 4,921,478 A | 5/1990 | Solano | |
| 4,964,849 A | 10/1990 | Robicsek | |
| 5,135,492 A | 8/1992 | Melker et al. | |
| 5,203,769 A | 4/1993 | Clement et al. | |
| 5,230,704 A | 7/1993 | Moberg et al. | |
| 5,269,768 A | 12/1993 | Cheung | |
| 5,707,356 A | 1/1998 | Paul | |
| 5,833,650 A | 11/1998 | Imran | |
| 5,902,264 A | 5/1999 | Toso et al. | |
| 6,142,980 A | 11/2000 | Schalk | |
| 6,712,815 B1 * | 3/2004 | Sampson et al. | 606/41 |

* cited by examiner

*Primary Examiner*—Sharon Kennedy
(74) *Attorney, Agent, or Firm*—Kevin J. Boland (57) ABSTRACT

The present invention is directed to a proximal catheter assembly that is configured to facilitate natural or suction-assisted aspiration through a catheter lumen. The proximal catheter assembly comprises a relief valve configured to regulate the level of suction-assisted aspiration provided through the working lumen of the catheter. When the level of suction-assisted aspiration exceeds a predetermined threshold, the relief valve opens to allow fluid to be drawn from tubing coupled to the proximal catheter assembly, thereby mitigating the relatively high levels of aspiration imposed upon the working lumen and the patient's vessel.

23 Claims, 8 Drawing Sheets

PROXIMAL CATHETER ASSEMBLY HAVING A RELIEF VALVE

CROSS-REFERENCE TO RELATED APPLICATIONS

This application is a continuation-in-part application of U.S. patent application Ser. No. 10/112,807, now U.S. Pat. No. 6,960,189 filed Mar. 29, 2002.

FIELD OF THE INVENTION

The present invention relates to an improved proximal catheter assembly, and more specifically, a catheter handle that is configured to provide a lumen of a catheter with substantially continuous natural aspiration and, optionally, suction-assisted aspiration that may be regulated using a relief valve.

BACKGROUND OF THE INVENTION

Today there is a growing need to provide controlled access and vessel management during such procedures as stenting, atherectomy or angioplasty. Generally during these procedures there is a high opportunity for the release of embolic material. The emboli may travel downstream from the occlusion, lodging deep within the vascular bed and causing ischemia. The resulting ischemia may pose a serious threat to the health or life of a patient if the blockage forms in a critical area, such as the heart, lungs, or brain.

Several previously known methods and apparatus incorporate the use of an external suction system in conjunction with an aspiration catheter for removal of the clot and/or removal of embolic particles. However, several disadvantages arise when using an external suction system as the sole means for flow management within a vessel. First, it may be difficult to establish the proper aspirating pressure required at the treatment site, and external pressure adjustments used with suction pumps may lead to an incorrect amount of suction for a given set of circumstances. If the amount of suction is too low for the circumstances, then embolic particles may not be effectively removed and may travel downstream from the original occlusion, leading to further occlusive events. If the amount of suction is too high, the vessel may collapse.

Moreover, if an external suction pump is utilized, retrieval of downstream emboli may require a flow rate that cannot be sustained by the vessel wall for more than a few seconds, resulting in insufficient removal of emboli. Additionally, continuous use of an external suction pump may result in excessive blood loss, requiring infusion of non-autologous blood and raising related safety issues.

Other methods for embolic removal have relied on more natural aspirating effects. For example, previously known devices have relied on the pressure differential between the atmosphere and blood flow in a treatment vessel to cause a reversal of flow in the treatment vessel. However, such natural aspiration techniques may provide insufficient flow to effectively remove emboli.

In view of these drawbacks of previously known systems, it would be desirable to provide a proximal catheter assembly that allows a catheter to achieve a substantially continuous level of natural, physiologically-regulated aspiration through a working lumen of the catheter.

It also would be desirable to provide a proximal catheter assembly that provides an appropriate level of retrograde flow at a treatment site to direct dislodged particles into a catheter for efficient removal without damaging the treatment vessel.

It further would be desirable to provide a proximal catheter assembly that provides an external suction/infusion port that selectively may be used, in conjunction with natural aspiration techniques, to further influence flow in a treatment vessel.

It still further would be desirable to provide a proximal catheter assembly that allows emboli to be filtered and blood reperfused into a patient's vessel to reduce blood loss.

It also would be desirable to provide a proximal catheter assembly that is configured to minimize "back-bleed" that occurs when flow exits through a hemostatic port disposed at the proximal end of a catheter.

It also would be desirable to provide a proximal catheter assembly having a relief valve that is configured to regulate the level of suction-assisted aspiration that may be provided through the working lumen of the catheter.

SUMMARY OF THE INVENTION

In view of the foregoing, it is an object of the present invention to provide a proximal catheter assembly that allows a catheter to achieve a substantially continuous level of natural, physiologically-regulated aspiration through a working lumen of the catheter.

It is also an object of the present invention to provide a proximal catheter assembly that provides an appropriate level of retrograde flow at a treatment site to direct dislodged particles into a catheter for efficient removal, without damaging the treatment vessel.

It is a further object of the present invention to provide a proximal catheter assembly that provides an external suction/infusion port that selectively may be used, in conjunction with natural aspiration techniques, to further influence flow in a treatment vessel.

It is yet a further object of the present invention to provide a proximal catheter assembly that allows emboli to be filtered and blood reperfused into a patient's vessel to reduce blood loss.

It is a further object of the present invention to provide a proximal catheter assembly that is configured to minimize "back-bleed" that occurs when flow exits through a hemostatic port disposed at the proximal end of a catheter.

It is yet another object of the present invention to provide a proximal catheter assembly having a relief valve that is configured to regulate the level of suction-assisted aspiration that may be provided through the working lumen of the catheter.

These and other objects of the present invention are accomplished by providing a proximal catheter assembly that is configured to enable two types of aspiration through a catheter lumen. The proximal catheter assembly enables a substantially continuous level of natural, physiologically-regulated aspiration through the catheter lumen using an arterial-venous shunt and, optionally, suction-assisted aspiration through the catheter lumen. This allows a physician to provide a substantially continuous level of retrograde flow in a treatment vessel during a medical procedure, while providing an external suction/infusion port that selectively may be used to further influence the level of aspiration within the vessel. In addition, the suction/infusion port may be used to selectively provide an antegrade flow, e.g., of a therapeutic drug or lytic agent.

In a first embodiment, a proximal catheter assembly of the device of the present invention comprises a handle that is coupled to a catheter, so that a working lumen of the catheter is in fluid communication with a bore of the handle. The handle preferably comprises an external suction/infusion port and at least one hemostatic port, each of which are in fluid communication with the working lumen of the catheter. The handle also is coupled to a blood outlet port that is in fluid communication with the working lumen, and preferably further comprises an inflation port that is in fluid communication with an inflation lumen of the catheter.

In use, the blood outlet port coupled to the handle may be coupled to a venous return line, which is adapted to be disposed in a remote vein. When the venous return line is disposed in the remote vein, and when an occlusive element of the catheter is deployed in a patient's artery, a pressure differential between venous and arterial pressure will cause blood to flow in a retrograde fashion in the artery. Specifically, blood in the artery flows into the working lumen, through the outlet port, and then through the venous return line, where it then is reperfused into the remote vein. A filter may be disposed between the outlet port and the venous return line to remove any emboli prior to reperfusing blood into the remove vein.

This natural, physiologically-regulated aspiration through the outlet port coupled to the catheter handle preferably occurs before, during and after a medical procedure performed through the working lumen of the catheter to effectively remove thrombi and/or emboli from the vessel. Additional suction selectively may be applied by coupling a syringe to the external suction/infusion port, to further influence aspiration of the vessel. Alternatively, the syringe may be used to infuse saline, drugs or other therapeutic agents to the treatment site. The hemostatic port coupled to the handle allows for the delivery of angioplasty, stent delivery systems or other devices to the treatment site.

In an alternative embodiment of the present invention, the proximal catheter assembly further comprises a handle having a roller clamp valve. The roller clamp valve may be used to selectively inhibit flow through the handle, so that "backbleed" from the catheter lumen through the hemostatic port is reduced.

In a preferred embodiment of the present invention, a proximal catheter assembly is provided that comprises a relief valve configured to regulate the level of suction-assisted aspiration that may be provided through the working lumen of the catheter. When the level of suction-assisted aspiration exceeds a predetermined threshold, the relief valve opens to allow blood to be drawn from tubing coupled to the venous return line. Using this technique, relatively high levels of suction-assisted aspiration will not be imposed upon the working lumen and the patient's vessel, but rather will be mitigated by the relief valve.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention is directed to a proximal catheter assembly that is configured to enable natural aspiration through a catheter lumen and, optionally, suction-assisted aspiration or infusion through the catheter lumen. The proximal catheter assembly of the present invention enables a substantially continuous level of natural, physiologically-regulated aspiration through the lumen of the catheter by enabling fluid communication between the lumen of the catheter and a patient's venous vasculature. The proximal catheter assembly also provides an external suction/infusion port that may be used in conjunction with a syringe, so that a physician further may influence the level of aspiration through the lumen of the catheter. The provision of substantially continuous retrograde flow and, optionally, selectively increased levels of retrograde flow at a treatment site facilitates removal of emboli during an interventional procedure while minimizing trauma to the treatment vessel. The proximal catheter assembly preferably is provided with a relief valve configured to regulate the level of suction-assisted aspiration that may be provided through the working lumen of the catheter.

Figure 1:
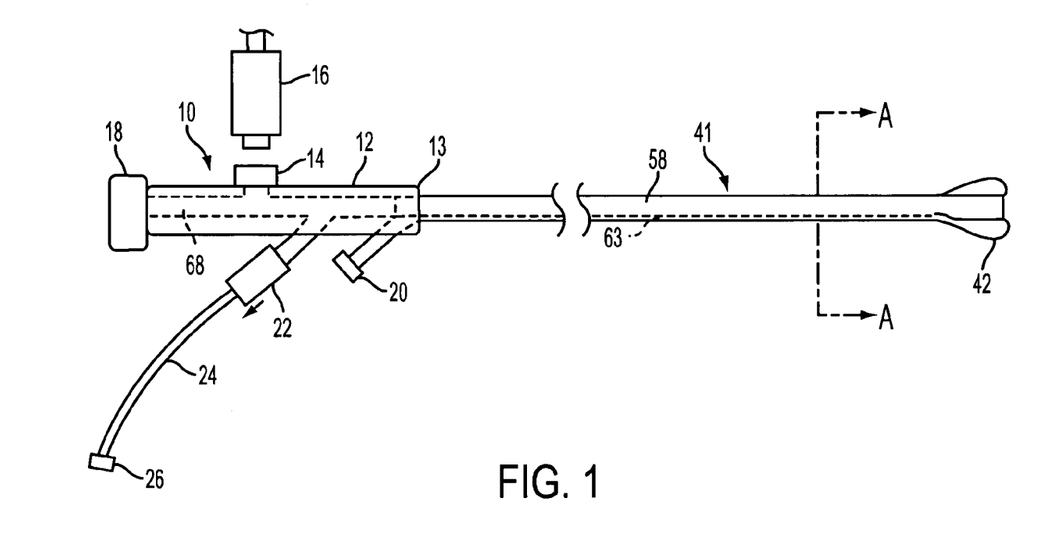
FIG. 1 provides a top sectional view of a proximal catheter assembly in accordance with principles of the present invention.

Referring to FIG. 1, a top sectional view of a proximal catheter assembly constructed in accordance with principles of the present invention is described. Proximal catheter assembly 10 is coupled to catheter 41 having proximal and distal ends and working lumen 58 extending therebetween. Proximal catheter assembly 10 comprises handle 12 having proximal and distal ends, and bore 68 extending therebetween. The proximal end of catheter 41 preferably is affixed within bore 68 near distal end 13 of handle 12, so that working lumen 58 of catheter 41 and bore 68 of handle 12 are in fluid communication with each other.

Handle 12 comprises external suction/infusion port 14, which is in fluid communication with bore 68 and working lumen 58 of catheter 41. External suction/infusion port 14 is configured to receive syringe 16, which may be used to induce enhanced aspiration or infusion through working lumen 58.

Handle 12 preferably further comprises inflation port 20, which is in fluid communication with inflation lumen 63 of catheter 41. Inflation lumen 63 further is in fluid communication with occlusive element 42, e.g., a balloon that is disposed at the distal end of catheter 41, so that occlusive element 42 may be deployed via inflation port 20 and inflation lumen 63.

Handle 12 is coupled to blood outlet port 26, which in turn preferably is coupled to a venous return line (not shown) that is adapted to be inserted into a patient's venous vasculature. In a preferred embodiment, one-way check valve 22 is disposed between handle 12 and blood outlet port 26, as shown in FIG. 1, to ensure that flow through the valve occurs exclusively in the direction indicated. For example, when flow is aspirated through catheter 41 via working lumen 58, that flow may enter and pass through one-way check valve 22, then flow through optional tubing 24 and through blood outlet port 26. However, one-way check valve 22 will not allow flow to occur through the valve in an opposite direction, i.e., from blood outlet port 26 into working lumen 58. For example, one-way check valve 22 may close when suction is being provided via syringe 16 to ensure that flow from blood outlet port 26 does not re-enter bore 68 and/or working lumen 58.

Handle 12 of proximal catheter assembly 10 further is coupled to at least one hemostatic port 18, e.g., a Touhy-Borst connector, which is per se known in the art. Hemostatic port 18, bore 68 and working lumen 58 of catheter 41 are sized to permit the advancement of conventional angioplasty catheters, stent delivery systems, thrombectomy systems, and other devices to a vascular treatment site via working lumen 58.

In accordance with principles of the present invention, proximal catheter assembly 10 may be used in conjunction with catheter 41 during a medical procedure to provide a substantially continuous level of natural, physiologically-regulated aspiration through working lumen 58 and, optionally, suction-assisted aspiration.

During the medical procedure, catheter 41 may be disposed in a patient's artery and occlusive element 42 may be deployed. The natural aspiration may be provided through working lumen 58 when a venous return line (not shown), which is coupled to blood outlet port 26, is introduced into a remote vein. Once this arterial-venous circuit is established, negative pressure in the venous line during diastole will establish a low rate continuous flow of blood through working lumen 58 of catheter 41, to the patient's vein via the venous return line. In effect, this arterial-venous shunt allows blood flow in the patient's artery that is distal of occlusive element 42 to flow in a retrograde fashion through working lumen 58, through one-way check valve 22, through outlet port 26, through the venous return line and back into the remote vein. This method, which utilizes the difference between venous and arterial pressure, may be used to provide a substantially continuous level of aspiration at a treatment site before, during and after a medical procedure, to ensure that emboli generated during the medical procedure are directed into working lumen 58 for safe removal. A filter (not shown) may be coupled between blood outlet port 26 and the venous return line so that emboli may be removed and filter blood reperfused into the venous vasculature.

With retrograde flow established in the selected artery via the venous return line, a medical procedure may be performed through hemostatic port 18 and working lumen 58. At any time before, during or after the medical procedure, additional aspiration may be provided at the treatment site via syringe 16. It is preferred that the additional suction provided by syringe 16 only is used in conjunction with the above-described natural aspiration technique for a limited period of time, e.g., at the time a vascular lesion is being traversed or disrupted, to ensure that trauma to the vessel wall due to the external suction is reduced. Alternatively, syringe 16 may be used to temporarily establish antegrade flow, e.g., to infuse contrast agents, drugs, lytic agents or other therapeutic agents.

Figure 2:
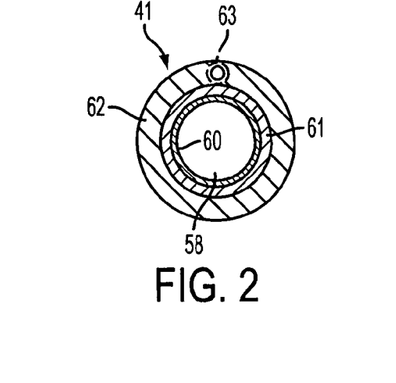
FIG. 2 provides a cross-sectional view along line A—A of FIG. 1.

Referring now to FIG. 2, a cross-section view along section A—A of FIG. 1 is provided. As shown in FIG. 2, catheter 41, which may be used in conjunction with proximal catheter assembly 10, preferably comprises inner layer 60 covered with a layer of flat stainless steel wire braid 61 and polymer cover 62. Inflation lumen 63 is disposed within polymer cover 62 and couples inflation port 20 to occlusive element 42. A proximal end of working lumen 58 is in fluid communication with external suction/infusion port 14, hemostatic port 18, and blood outlet port 26, as described hereinabove with respect to FIG. 1.

Figure 3A:
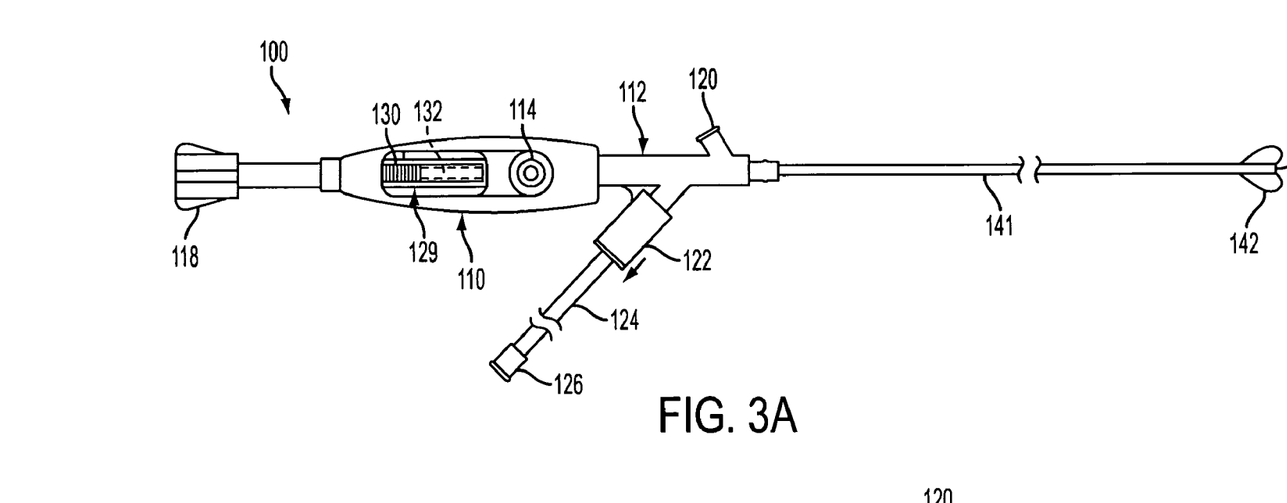
FIGS. 3A–3B are, respectively, a top view and a top sectional view of an alternative embodiment of the present invention.

Referring now to FIG. 3, an alternative proximal catheter assembly constructed in accordance with principles of the present invention is described. FIG. 3A provides a top view of proximal catheter assembly 100, which is coupled to catheter 141 having proximal and distal ends and working lumen 158 extending therebetween. Catheter 141 preferably is provided in accordance with catheter 41 of FIGS. 1–2.

Figure 3B:
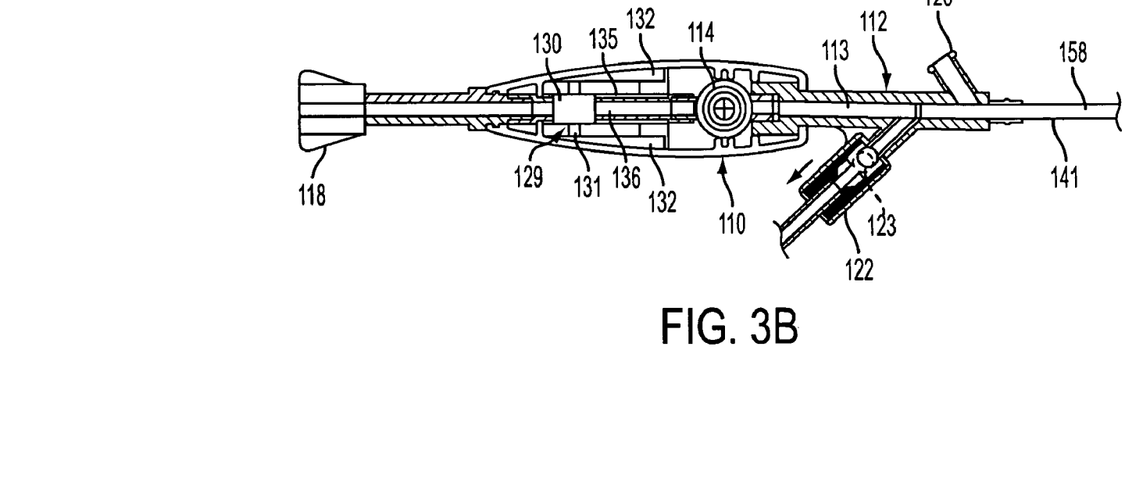
Figure 4A:
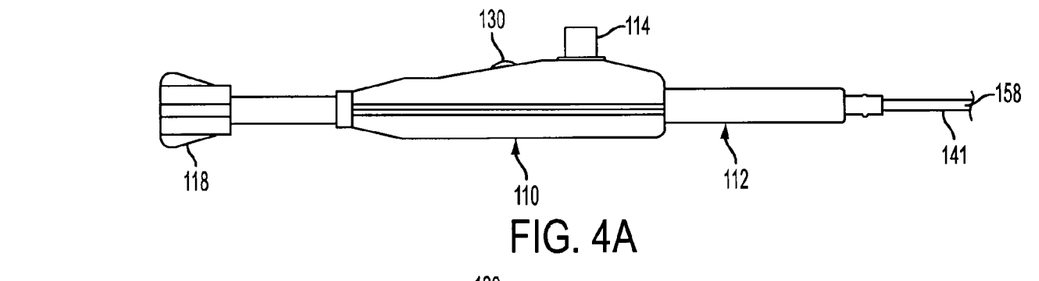
FIGS. 4A–4C are, respectively, a side view and side sectional views of the proximal catheter assembly of FIG. 3.

Proximal catheter assembly 100 preferably comprises handle 110 and hub 112, each having proximal and distal ends. The distal end of hub 112 is configured to receive and sealingly engage the proximal end of catheter 141, as shown in a top sectional view in FIG. 3B. Working lumen 158 of catheter 141 is in fluid communication with bore 113 of hub 112, which in turn is in fluid communication with lumen 136 of tubing 135, as described in detail with respect to FIG. 4 hereinbelow.

Proximal catheter assembly 100 further comprises inflation port 120, which preferably is coupled to hub 112 and is in fluid communication with an inflation lumen of catheter 141, e.g., inflation lumen 63 of FIG. 1. The inflation lumen of catheter 141 further is in fluid communication with occlusive element 142 disposed at the distal end of catheter 141, so that occlusive element 142 may be deployed via inflation port 120 and the inflation lumen.

Hub 112 of proximal catheter assembly 100 further is coupled to blood outlet port 126, which in turn is coupled to a venous return line (not shown) that is adapted to be inserted into a patient's venous vasculature, as described hereinabove. In a preferred embodiment, one-way check valve 122 is disposed between distal hub 112 and blood outlet port 126 to ensure that flow through one-way check valve 122 occurs only in the direction indicated. As shown in FIG. 3B, one-way check valve 122 preferably comprises ball 123 that is configured to plug an opening of one-way check valve 122, if necessary, to prevent flow from occurring from outlet port 126 into bore 113 and/or working lumen 158.

Figure 4B:
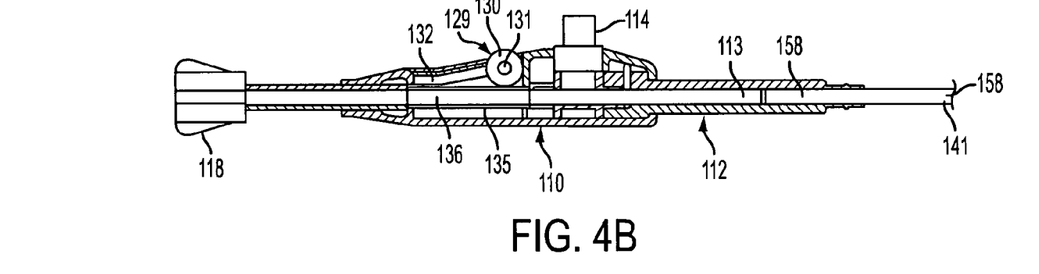
Figure 4C:
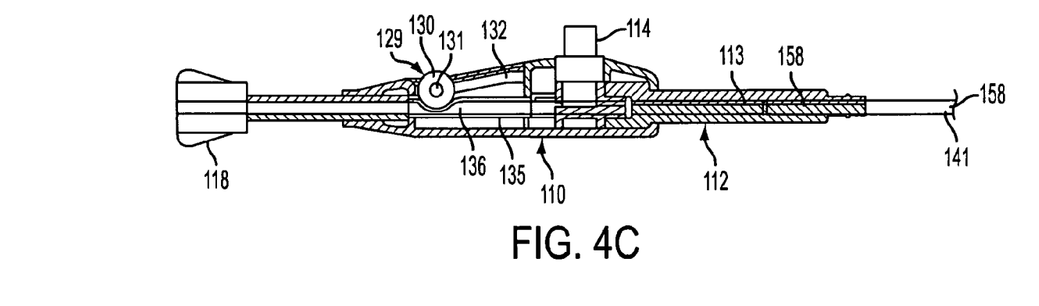

External suction/infusion port 114 is in fluid communication with working lumen 158 of catheter 141, as shown in FIGS. 4B–4C. External suction/infusion port 114 is configured to provide external suction through working lumen 158 when a syringe is coupled to port 114. Alternatively, as described hereinabove with respect to port 14 of the embodiment of FIG. 1, port 114 may be used to infuse fluid into the vessel.

Handle 110 further comprises at least one hemostatic port 118 that is in fluid communication with working lumen 158 of catheter 141. Hemostatic port 118 and working lumen 158 are sized to permit the advancement of conventional angioplasty catheters, stent delivery systems, and thrombectomy systems to a vascular treatment site via working lumen 158. As shown in FIG. 3B, and also from side sectional views in FIGS. 4B–4C, handle 110 further comprises a section of tubing 135 that is disposed substantially within handle 110. Tubing 135 comprises lumen 136 that is in fluid communication with hemostatic port 118, external suction/infusion port 114, bore 113 of hub 112 and working lumen 158 of catheter 141.

Handle 110 further comprises roller clamp valve 129, which is configured to selectively inhibit flow through handle 110. Roller clamp valve 129 preferably comprises roller clamp 130 that is mounted on shaft 131, whereby shaft 131 is configured for longitudinal motion within angled slot 132, as shown from a top sectional view in FIG. 3B and from side sectional views in FIGS. 4B–4C. Angled slot 132 is disposed within a portion of handle 110 and tapers from a proximal point in which it is substantially adjacent to tubing 135, as shown in FIG. 4B, to a distal point in which it is further away from tubing 135, as shown in FIG. 4C.

When roller clamp 130 is provided in a distal position within angled slot 132, it will not inhibit fluid transfer occurring within lumen 136 of tubing 135, as shown in FIG. 4B. However, when roller clamp 130 is disposed in a proximal position within angled slot 132, as shown in FIG. 4C, it impinges upon tubing 135 and inhibits flow within lumen 136. In effect, roller clamp valve 129 serves as a switch that allows a physician to selectively inhibit fluid transfer between working lumen 158 of catheter 141 and hemostatic port 118. By inhibiting flow through lumen 136 of tubing 135, roller clamp valve 129 may prevent "back-bleed" from occurring when hemostatic port 118 is open, e.g., when catheter 141 is advanced over a guidewire to a treatment site.

In accordance with principles of the present invention, proximal catheter assembly 100 then may be used in conjunction with catheter 141 during a medical procedure to provide a substantially continuous level of natural aspiration and, optionally, syringe-assisted aspiration via external suction/infusion port 114. The preferred method for obtaining the substantially continuous level of natural aspiration using proximal catheter assembly 100 is the same technique described hereinabove with respect to proximal catheter assembly 10 of FIG. 1, which disposes a venous return line in a remote vein and utilizes the difference between venous and arterial pressure to achieve retrograde flow at a treatment site.

Figures 5A, 5B, 5C, 5D:
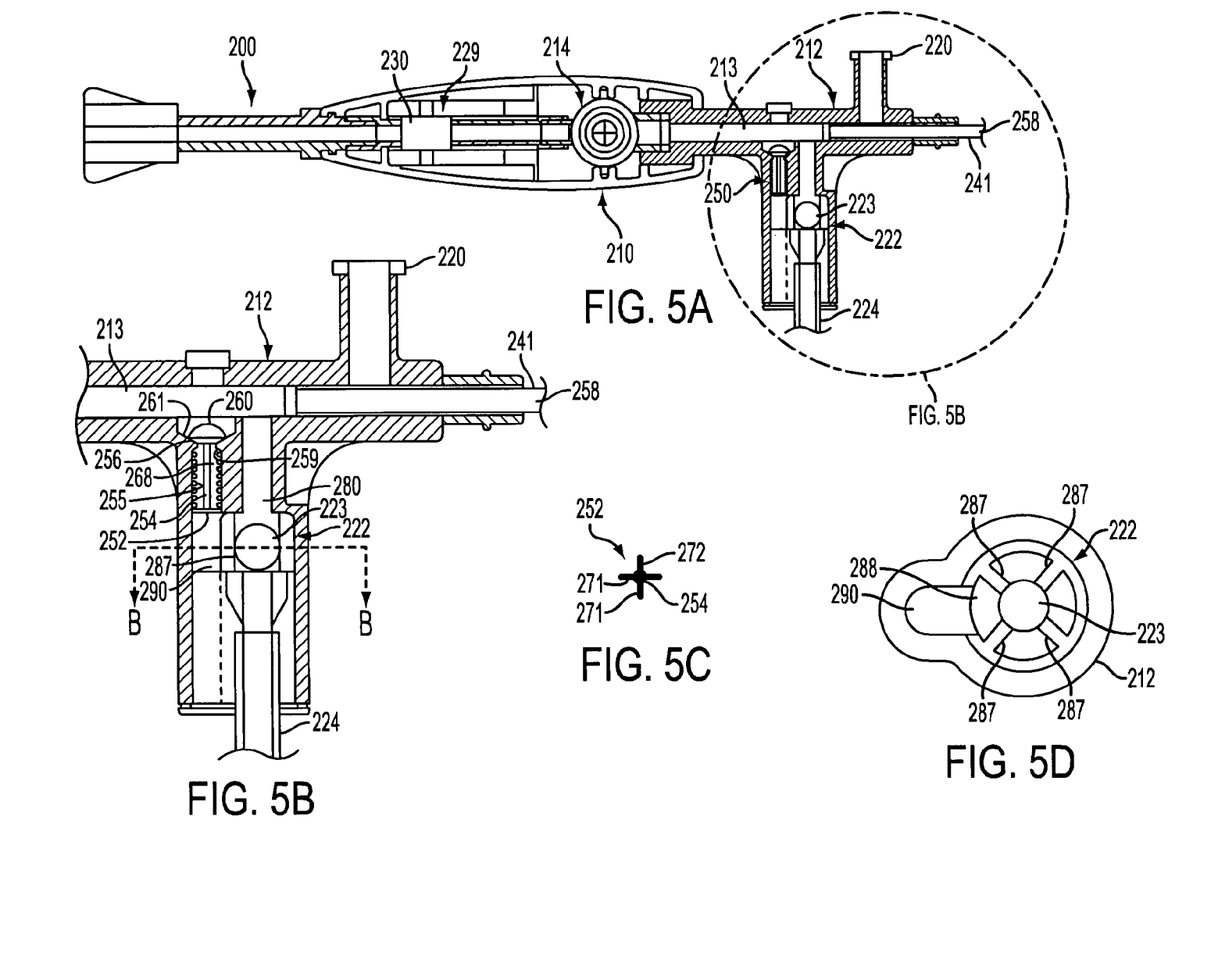
FIGS. 5A–5D describe a proximal catheter assembly having a relief valve.

Referring now to FIGS. 5A–6C, features of a relief valve provided in accordance with principles of the present invention are described. In FIG. 5A, proximal catheter assembly 200 preferably is constructed in accordance with proximal catheter assembly 100 of FIGS. 3A–4C, except as noted below.

FIG. 5A provides a top sectional view of proximal catheter assembly 200, which is coupled to catheter 241 having proximal and distal ends and working lumen 258 extending therebetween. Catheter 241 preferably is constructed as described hereinabove with respect to catheter 41 of FIGS. 1–2.

Proximal catheter assembly 200 preferably comprises handle 210 and hub 212, each having proximal and distal ends. Working lumen 258 of catheter 241 is in fluid communication with bore 213 of hub 212, which in turn is in fluid communication with handle hub 210, as described hereinabove with respect to the embodiment of FIG. 4. Handle 210 preferably further comprises inflation port 220. Hub 212 of proximal catheter assembly 200 further is coupled to tubing 224, which in turn preferably is coupled to a venous return line (not shown) that is adapted to be inserted into a patient's venous vasculature, as described hereinabove.

External suction/infusion port 214 is in fluid communication with working lumen 258 of catheter 241, as described in FIGS. 4B–4C hereinabove. External suction/infusion port 214 is configured to provide external suction through working lumen 258 when a syringe is coupled to port 214. Alternatively, port 214 may be used to infuse fluid into the vessel.

In the embodiment of FIG. 5A, relief valve 250 is provided to regulate the amount of suction-assisted aspiration provided by suction/infusion port 214. In particular, when the level of suction-assisted aspiration provided by suction/infusion port 214 exceeds a predetermined threshold, relief valve 250 "opens," as described in detail hereinbelow, to allow blood to be drawn from tubing 224, which is coupled to the venous return line. Therefore, relatively high levels of suction-assisted aspiration will not be imposed upon working lumen 258 and the patient's vessel, but rather will be mitigated by drawing blood from tubing 224, as described with respect to FIGS. 6A–6C hereinbelow.

Referring now to FIG. 5B, a detailed top sectional view of relief valve 250 of FIG. 5A is provided. Relief valve 250 comprises base 252, head 260, and rod 254 that couples base 252 to head 260. Base 252 is disposed within channel 268 of hub 212, as shown in FIG. 5B. In FIG. 5C, base 252 is shown in detail from a side sectional view as comprising plurality of struts 271 affixed to rod 254. Apertures 272 are formed between struts 271 and an interior surface of channel 268, thereby allowing blood to flow from tubing 224 into channel 268, as described hereinbelow.

End portion 259 of channel 268 comprises a reduced inner diameter relative to a main inner diameter of channel 268, and forms tapered seat 261 against which head 260 is urged by helical spring 255. One end of spring 255 engages end portion 259 of channel 268, while the other end of spring 255 engages struts 271 of base 252.

A transition between channel 268 and bore 213 of hub 212 defines tapered seat 261. Head 260 of relief valve 250 preferably comprises tapered seal 256, as shown in FIG. 5B, that sealingly engages tapered seat 261 under bias of spring 255, thus inhibiting fluid communication between bore 213 and channel 268 in the closed state.

Proximal catheter assembly 200 further preferably comprises one-way check valve 222. One-way check valve 222 functions as described hereinabove with respect to one-way check valve 122 of FIG. 3B, and preferably is disposed between bore 280, which is in fluid communication with bore 213 and working lumen 258, and tubing 224, which is in fluid communication with the venous return line.

Referring to FIG. 5D, a cross-sectional view across line B—B of FIG. 5B is described. One-way check-valve 222 preferably comprises ball 223 that is contained within plurality of ball guides 287, which allow longitudinal movement of ball 223 within the valve. Apertures 288 are formed between ball guides 287, ball 223 and an exterior surface of one-way check valve 222. When flow occurs in a direction from working lumen 258 toward tubing 224 via bore 280, apertures 288 allow flow to be channeled into tubing 224. However, ball 223 is configured to plug an opening into bore 280 to prevent flow from occurring from tubing 224 into bore 213 and/or working lumen 258.

Although blood may not flow from tubing 224 into bore 213 and/or working lumen 258 via bore 280, blood may flow from tubing 224 into channel 268 at certain times, i.e., when a predetermined threshold of suction-assisted aspiration has been exceeded, as described in detail with respect to FIG. 6C hereinbelow. In this scenario, blood flows from tubing 224, through apertures 288, through region 290, and through apertures 272 of base 252 and channel 268.

Figure 6A:
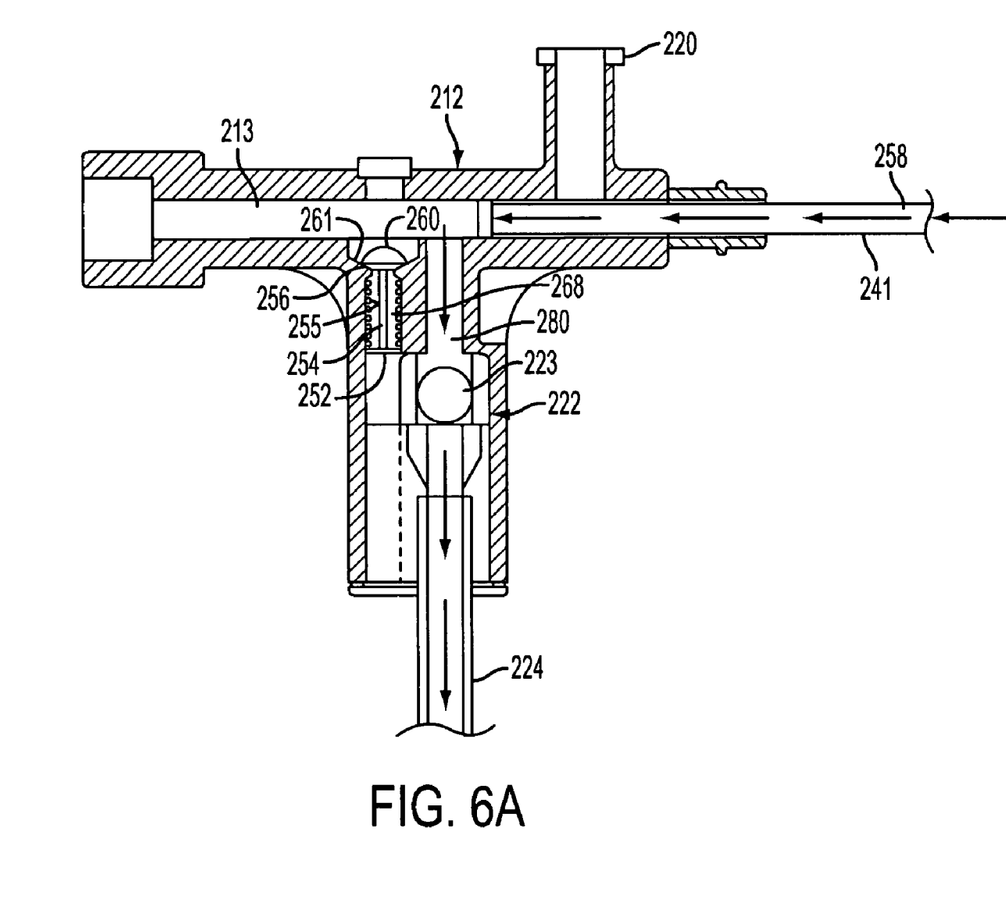
FIGS. 6A–6C illustrate a method of using the relief valve of FIGS. 5A–5D.
Figure 6B:
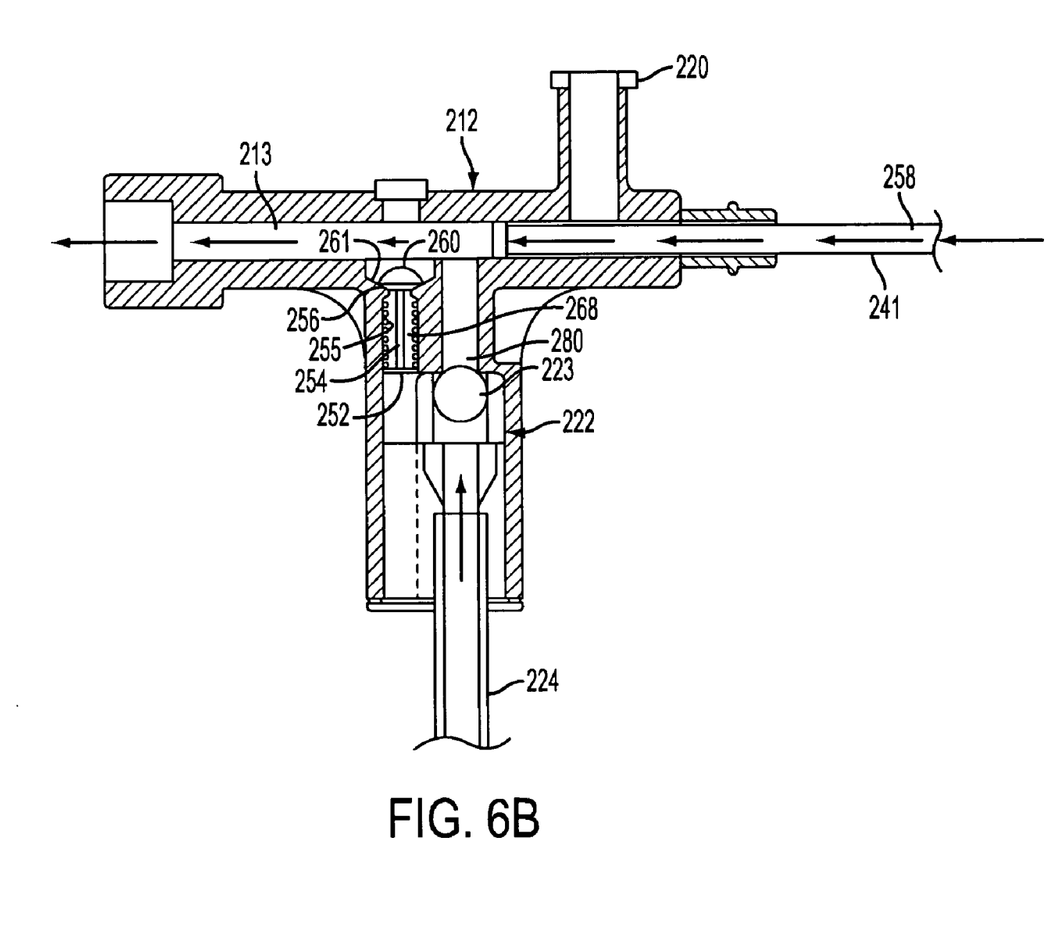
Figure 6C:
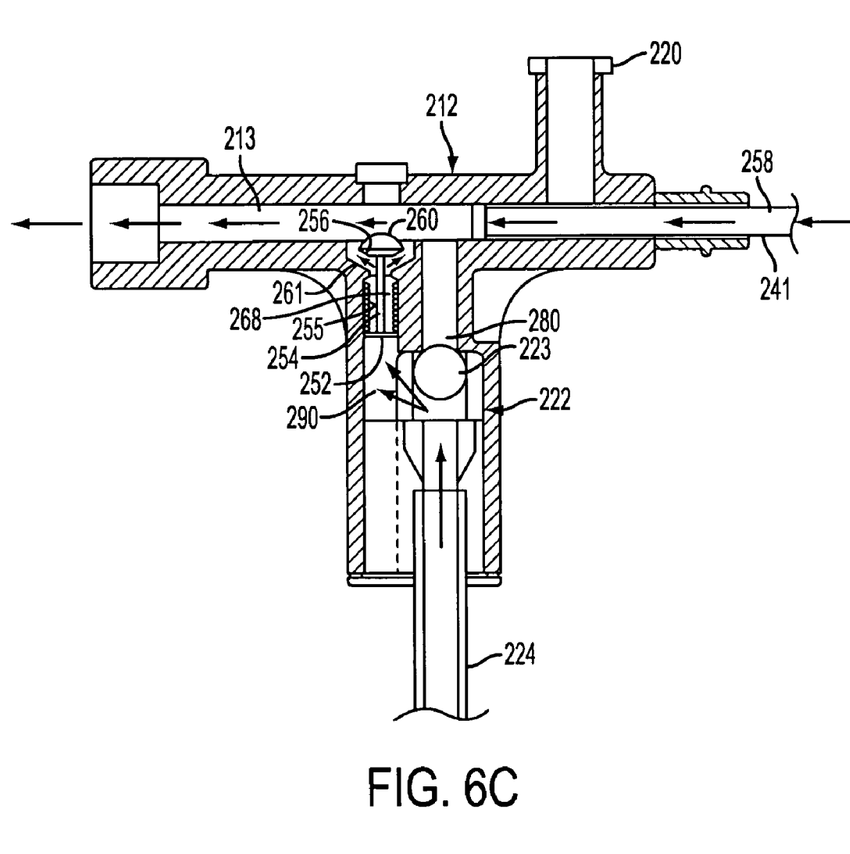

Referring now to FIGS. 6A–6C, a detailed description of the operation of relief valve 250 is provided. In FIG. 6A, the arrows indicate the direction in which blood flows when the natural, physiologically-regulated flow is provided through lumen 258 of catheter 241.

Specifically, in a preferred embodiment, catheter 241 is disposed in a patient's artery and occlusive element 42 of FIG. 1 may be deployed. The natural aspiration may be provided through working lumen 258 when a venous return line (not shown), which is coupled tubing 224, is introduced into a remote vein. Once this arterial-venous circuit is established, negative pressure in the venous line during diastole will establish a low rate continuous flow of blood through working lumen 258 of catheter 241, to the patient's vein via the venous return line. In effect, this arterial-venous shunt allows blood flow in the patient's artery that is distal of occlusive element 42 to flow in a retrograde fashion through working lumen 258, through bore 280, through apertures 288 of one-way check valve 222, into tubing 224, through blood outlet port 26 of FIG. 1, through the venous return line and back into the remote vein. A filter (not shown) may be coupled between blood outlet port 26 of FIG. 1 and the venous return line so that emboli may be removed and filter blood reperfused into the venous vasculature.

During the period in which a relatively low level of natural, physiologically-regulated flow is provided through tubing 224, spring 255 causes relief valve 250 to remain in a closed position, i.e., whereby tapered seal 256 of head 260 sealingly engages tapered seat 261. This is because, when no substantial external forces are exerted on spring 255, spring 255 biases head 260 against tapered seat 261.

Referring now to FIG. 6B, operation of relief valve 250 is described where a physician applies a relatively low or moderate level of suction-assisted aspiration via external suction/infusion port 214, e.g., using a syringe. The suction-assisted aspiration causes flow to occur in the direction indicated by the arrows in FIG. 6B. When the suction-assisted aspiration is applied, ball 223 of one-way check valve 222 moves toward bore 280 to plug an opening into bore 280. This ensures that fluid is not aspirated from tubing 224, but rather from working lumen 258 and the patient's vasculature.

When a relatively low or moderate level of suction-assisted aspiration is applied, i.e., a level that will not generally cause damage to a patient's vessel, relief valve 250 may still remain in the closed position whereby tapered seal 256 of head 260 sealingly engages tapered seat 261. Relief valve 250 may remain in the closed position with relatively low or moderate levels of suction-assisted aspiration because the suction force imposed upon head 260 does not overcome the resistance force provided by spring 255, i.e., spring 255 remains in an expanded state wherein tapered seal 256 engages tapered seat 261.

Referring now to FIG. 6C, a relatively high level of suction-assisted aspiration has been introduced via external suction/infusion port 214. The relatively high level of suction-assisted aspiration causes flow through bore 213 to exert a suction force upon head 260 that exceeds the resistance force provided by spring 255. This causes head 260 of relief valve 250 to be drawn toward bore 213, which in turn causes base 252 of relief valve 250 to be urged in the same direction. When base 252 is urged in a direction toward bore 213, struts 271 of base 252 engage spring 255 and cause spring 255 to be compressed, as shown in FIG. 6C.

The relatively high level of suction-assisted aspiration causes relief valve to assume an open state, i.e., where tapered seal 256 is not sealingly engaged with tapered seat 261. This form a gap in which blood may flow between channel 268 and bore 213, as indicated by the arrows in FIG. 6C.

In the open state, relief valve 250 allows blood to be partially drawn from tubing 224, which preferably is coupled to a patient's venous vasculature. Specifically, blood flows from tubing 224, through apertures 288 of FIG. 5D (of one-way check-valve 222), through region 290, through apertures 272 of base 252, and into channel 268. Blood then is drawn from channel 268 into bore 213 via the gap provided between tapered seal 256 and tapered seat 261.

Advantageously, when the suction-assisted aspiration provided by external suction/infusion port 214 is relatively high, relief valve 250 opens and blood is at least partially drawn from tubing 224, which reduces the blood drawn from working lumen 258 and the patient's vessel. By mitigating the level of relatively high suction-assisted aspiration imposed on the patient's vessel using relief valve 250, damage to the patient's vessel can be reduced.

It should also be appreciated by those skilled in the art that relief valve 250 of the present invention may be used when apparatus 200 exclusively has a potential for suction-assisted aspiration, and is not capable of the natural, physiologically-regulated aspiration described hereinabove. In this case, for example, tubing 224 may be coupled to a fluid source, e.g., saline, in lieu of being coupled to the venous return line. Then, saline will be drawn through tubing 224, into channel 268 and through bore 213 to mitigate the suction-assisted aspiration level imposed within working lumen 258.

It should also be appreciated by those skilled in the art that relief valve 250 of the present invention may be used when apparatus 200 exclusively has a potential for suction-assisted aspiration, and is not capable of the natural, physiologically-regulated aspiration described hereinabove. In this case, for example, tubing 224 may be coupled to a fluid source, e.g., saline, in lieu of being coupled to the venous return line or the atmosphere. Then, saline will be drawn through tubing 224, into channel 268 and through bore 213 to mitigate the suction-assisted aspiration level imposed within working lumen 258. Similarly, relief valve 250 of FIG. 5A may be used where tubing 224 is open to atmospheric pressure, in which case air will be drawn through channel 268 and bore 213 to mitigate the aspiration level imposed within working lumen 258.

Figure 7:
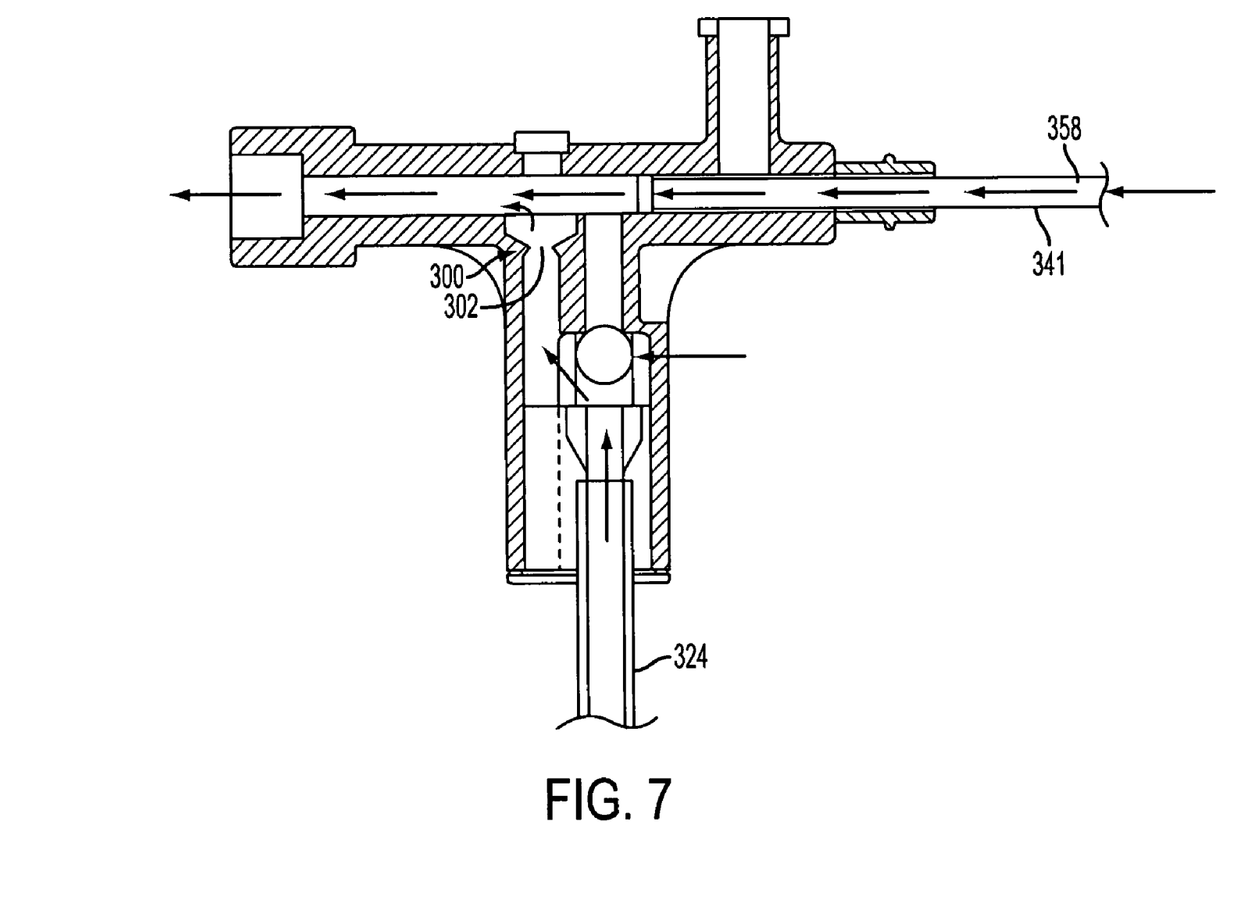
FIG. 7 describes an alternative embodiment of the relief valve of FIGS. 5A–6C.

In an alternative embodiment of relief valve 250, the components described in FIGS. 5A–6C may be replaced by a single orifice, as shown in FIG. 7. In FIG. 7, relief valve 300 comprises orifice 302 that allows relatively small levels of blood or fluid to be drawn from tubing 324 when relatively low or moderate suction-assisted aspiration is applied. However, when relatively high levels of suction-assisted aspiration are applied, higher levels of blood or fluid may be drawn from tubing 324 via orifice 302, which in effect will mitigate the level of aspiration imposed within working lumen 358 of catheter 341, and thereby reduce trauma imposed on a patient's vessel. In the embodiment of FIG. 7, it will be understood by those skilled in the art that the predetermined threshold for maximum amount of suction-assisted aspiration may be determined by selectively sizing an inner diameter of orifice 300 prior to the procedure.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

The invention claimed is:

1. Apparatus comprising:
   a hub having a distal end, a blood outlet port, an aspiration port, and a bore in fluid communication with the blood outlet port and the aspiration port;
   a catheter having a proximal end, a distal end, a working lumen extending therebetween, and a single inflatable member located at the distal end of the catheter;

wherein the distal end of the hub receives and is sealingly engaged with the proximal end of the catheter so that the bore is in fluid communication with the working lumen of the catheter; and a relief valve disposed within the hub and configured to regulate the level of suction-assisted aspiration provided to the working lumen of the catheter.

2. The apparatus of claim 1 wherein the relief valve is configured to provide partial communication between the blood outlet port and the aspiration port when an aspiration threshold is exceeded.

3. The apparatus of claim 1 wherein the relief valve comprises a base and a head, and a rod disposed therebetween, wherein the base is disposed within a channel of the hub.

4. The apparatus of claim 3 wherein the base further comprises a plurality of struts affixed to the rod, wherein a plurality of apertures are formed between the struts and an interior wall of the channel.

5. The apparatus of claim 4 wherein an end portion of the channel comprises a reduced inner diameter relative to a main inner diameter of the channel.

6. The apparatus of claim 5 further comprising a spring that biases the relief valve to a closed position.

7. The apparatus of claim 6 wherein the spring is provided with a predetermined resistance force that is proportional to a desired suction-assisted aspiration threshold.

8. The apparatus of claim 3 further comprising a tapered seat provided between the channel and the bore of the hub.

9. The apparatus of claim 8 wherein the head of the relief valve further comprises a tapered seal, wherein the tapered seal is configured to sealingly engage the tapered seat in a closed state.

10. The apparatus of claim 1 further comprising a one-way check valve disposed to regulate flow through the blood outlet port.

11. The apparatus of claim 10 wherein the one-way check valve causes flow to occur exclusively in a direction from the bore into the blood outlet port.

12. The apparatus of claim 11 wherein the one-way check valve closes to inhibit flow through the one-way check valve when suction is applied via the aspiration port.

13. The apparatus of claim 10 wherein the one-way check valve comprises a ball that is contained within a plurality of ball guides.

14. The apparatus of claim 1 wherein the relief valve comprises a single orifice that is disposed between the blood outlet port and the aspiration port.

15. A method for regulating the level of suction-assisted aspiration provided to a working lumen of a catheter, the method comprising:

providing apparatus comprising a hub having a distal end, a blood outlet port, an aspiration port, a relief valve, and a bore in fluid communication with the blood outlet port, the relief valve, and the aspiration port, the distal end of the hub coupled to a catheter having a working lumen extending from its proximal end to its distal end and a single inflatable member located on the distal end of the catheter;

providing suction-assisted aspiration through the bore and the working lumen via the aspiration port;

causing the relief valve to open when a level of suction-assisted aspiration exceeds a predetermined threshold; and causing fluid from the blood outlet port to be directed through the relief valve and toward the aspiration port, if the level of suction-assisted aspiration exceeds a predetermined threshold.

16. The method of claim 14 further comprising providing a one-way check valve disposed between the bore and the blood outlet port, and actuating the one-way valve to cause flow exclusively in a direction from the working lumen to the blood outlet port.

17. The method of claim 16 further comprising inhibiting fluid flow in a direction from the blood outlet port into the bore of the hub and working lumen when suction-assisted aspiration is provided via the aspiration port.

18. The apparatus of claim 1, wherein the bore, and the working lumen are sized to permit the advancement of conventional angioplasty catheters, stent delivery systems, and thrombectomy systems to a treatment site distal to the catheter via the working lumen.

19. The method of claim 15, wherein the bore and the working lumen are sized to permit the advancement of conventional angioplasty catheters, stent delivery systems, and thrombectomy systems to a treatment site distal to the catheter via the working lumen.

20. The apparatus of claim 1 wherein the catheter consists of only two lumens, an inflation lumen and the working lumen.

21. Apparatus comprising:

a hub having a distal end, a blood outlet port, an aspiration port, and a bore in fluid communication with the blood outlet port and the aspiration port;

a catheter having a proximal end, a distal end, with a single inflatable member located on the distal end, and a working lumen extending therebetween; wherein the distal end of the hub receives and is sealingly engaged with the proximal end of the catheter so that the bore is in fluid communication with the working lumen of the catheter; and a relief valve disposed within the hub and configured to regulate the level of suction-assisted aspiration provided to the working lumen of the catheter.

22. The apparatus of claim 21, wherein the catheter consists of only two lumens, an inflation lumen and the working lumen.

23. The apparatus of claim 21, wherein the bore and the working lumen are sized to permit the advancement of conventional angioplasty catheters, stent delivery systems, and thrombectomy systems to a treatment site distal to the catheter via the working lumen.

* * * * *

UNITED STATES PATENT AND TRADEMARK OFFICE
CERTIFICATE OF CORRECTION

| | |
|---|---|
| PATENT NO. | : 7,033,336 B2 |
| APPLICATION NO. | : 10/138013 |
| DATED | : April 25, 2006 |
| INVENTOR(S) | : Michael Hogendijk |

It is certified that error appears in the above-identified patent and that said Letters Patent is hereby corrected as shown below:

At column 12, claim 16: line 11: change "claim 14" to --claim 15--

Signed and Sealed this

Fifth Day of September, 2006

JON W. DUDAS
*Director of the United States Patent and Trademark Office*